(12) United States Patent
Kraus et al.

(10) Patent No.: US 9,439,694 B2
(45) Date of Patent: Sep. 13, 2016

(54) ELECTRICAL INTRAMEDULLARY NAIL SYSTEM

(75) Inventors: Werner Kraus, München (DE); Stephanie Kraus, Bad Tölz (DE); Markus Wiegmann, München (DE)

(73) Assignee: Neue Magnetodyn GmbH, München (DE)

( * ) Notice: Subject to any disclaimer, the term of this patent is extended or adjusted under 35 U.S.C. 154(b) by 1679 days.

(21) Appl. No.: 11/736,173

(22) Filed: Apr. 17, 2007

(65) Prior Publication Data

US 2007/0265628 A1    Nov. 15, 2007

(30) Foreign Application Priority Data

Apr. 19, 2006    (DE) .................. 10 2006 018 191

(51) Int. Cl.
| | |
|---|---|
| *A61B 17/72* | (2006.01) |
| *A61N 1/32* | (2006.01) |
| *A61N 1/40* | (2006.01) |
| *A61N 2/02* | (2006.01) |
| *A61N 2/06* | (2006.01) |

(52) U.S. Cl.
CPC ............... *A61B 17/72* (2013.01); *A61N 1/326* (2013.01); *A61N 1/40* (2013.01); *A61N 2/02* (2013.01); *A61N 2/06* (2013.01)

(58) Field of Classification Search
CPC ............. A61B 17/72–17/7291; A61C 8/0007; A61N 1/326
USPC ....... 606/62–68, 300–331; 623/23.16, 23.49, 623/24; 411/14; 433/173–176, 201.1, 215
See application file for complete search history.

(56) References Cited

U.S. PATENT DOCUMENTS

| | | | | |
|---|---|---|---|---|
| 5,030,236 A | * | 7/1991 | Dean .......................... | 623/23.49 |
| 5,292,252 A | * | 3/1994 | Nickerson et al. ........... | 433/173 |
| 5,725,377 A | * | 3/1998 | Lemler et al. ................ | 433/173 |

(Continued)

FOREIGN PATENT DOCUMENTS

| | | |
|---|---|---|
| CA | 244914 A1 | 4/2004 |
| CH | 618610 A5 | 1/1978 |

(Continued)

OTHER PUBLICATIONS

PCT Search Report PCT/DE2007/00640.

(Continued)

*Primary Examiner* — Jan Christopher Merene
*Assistant Examiner* — Steven Cotroneo
(74) *Attorney, Agent, or Firm* — The Dobrusin Law Firm, P.C.

(57) ABSTRACT

An intramedullary nail system including an elongated nail member comprising a cavity and electrically conductive at least in part, a coil assembly, a first electrode connected to a first pole of the coil assembly and a second electrode connected to a second pole of the coil assembly. To improve such an intramedullary nail system the coil assembly is provided in an end cap assembly that is proximally releasably connected to the nail member and with at least one electrically conductive outer contact surface. At least one section of the electrically conductive outer contact surface forms the first electrode and at least one section of the nail member forms the second electrode.

20 Claims, 7 Drawing Sheets

(56) References Cited

U.S. PATENT DOCUMENTS

| | | | |
|---|---|---|---|
| 6,034,295 A * | 3/2000 | Rehberg et al. | 623/23.49 |
| 6,224,601 B1 | 5/2001 | Friedl | |
| 6,416,516 B1 * | 7/2002 | Stauch et al. | 606/62 |
| 6,610,096 B2 * | 8/2003 | MacDonald | 623/18.11 |
| 6,778,861 B1 * | 8/2004 | Liebrecht et al. | 607/116 |
| 7,172,594 B2 * | 2/2007 | Biscup | 606/86 A |
| 7,389,140 B1 * | 6/2008 | Kroll | 607/9 |
| 7,615,070 B2 * | 11/2009 | Biscup | 606/322 |
| 2005/0055024 A1 * | 3/2005 | James et al. | 606/64 |
| 2005/0059972 A1 * | 3/2005 | Biscup | 606/73 |
| 2006/0004431 A1 * | 1/2006 | Fuller et al. | 607/116 |
| 2007/0265628 A1 | 11/2007 | Kraus | |
| 2008/0255556 A1 * | 10/2008 | Berger | 606/60 |
| 2010/0100188 A1 * | 4/2010 | Fuller et al. | 623/18.11 |

FOREIGN PATENT DOCUMENTS

| | | |
|---|---|---|
| DE | 2636818 | 2/1978 |
| DE | 2742741 A1 | 4/1979 |
| DE | 19709514 C1 | 11/1998 |
| EP | 0781532 A1 | 7/1997 |
| WO | 02/38082 | 5/2002 |
| WO | WO 02/38082 | 5/2002 |

OTHER PUBLICATIONS

European Search Report, EP1847227A1, published Apr. 2, 2007.
International Search Report, PCT/DE2007/00640, Jul. 23, 2007.

* cited by examiner

ELECTRICAL INTRAMEDULLARY NAIL SYSTEM

CLAIM OF BENEFIT OF EARLIER FILING DATE

The present application claims the benefit of the filing date of German Application No. DE 102006018191.3 (filed Apr. 19, 2006) the contents of which are hereby incorporated by reference in their entirety.

TECHNICAL FIELD

The invention relates to an intramedullary nail system including an elongated nail member comprising a cavity and which is electrically conductive at least in part, a coil assembly, a first electrode connected to a first pole of the coil assembly and a second electrode connected to a second pole of the coil assembly.

BACKGROUND OF THE INVENTION

Such intramedullary nail systems are known in the field of osteosynthesis which serves the fixation of fragments of a broken or diseased bone in its uninjured, natural form stable to loading by implanted screws, supporting plates, wires, intramedullary nails and the like which are generally made of stainless steel or titanium alloys. These osteosynthesis means permit speedy mobilization of the patient whilst resting the injured bone as is vital for its healing.

Problematic with a rigid fixation by comparatively unelastic, tissue-displacing supporting implants is, however, the hinderance to biological recuperation particularly due to the loss of blood vessels and nerves. Apart from this, the longer the implantation duration the more the biomechanical quality of the supporting structure suffers due to the partial withdrawal of its function. Loss of biological inspection increases, however, the risk of infection by resistant bacteria (MRSA=multiresistant *staphylococcus Aureus*) which, it has been shown, can colonize the surface of metal implants in the form of an adherent biofilm and withstand antibiotics by a mucuous sheath of polysaccharides.

These problems can be relieved in the scope of orthopedic surgery by magnetically induced electrical osteotherapy, for instance, in making use of the intramedullary nail systems as cited at the outset as described for example in DE 26 36 818 C2. In electrical osteotherapy low-frequency electrical AC potentials are induced in means of osteosynthesis by exposing the afflicted body part to a magnetic alternating field. Numerous clinical applications of this technique in the treatment of bone defects, cysts and tumor metastases chronically resistant to therapy and usually involving an infection as well as near-clinical experimental studies have long since shown that an optimum healing effect is achieved by using osteosynthesis implants as sources of extremely low-frequency sinusoidal AC potentials in the region of the bone adjoining the supportive metal.

The principle involved in transmission is the same as that of a transformer: the injured or diseased region of the body is flooded with a sinusoidal magnetic field of extremely low frequency in the range of approx. 1 to 100 Hz—preferably 4 to 20 Hz—and a magnetic flux density in the range of 0.5 to 5 mT (5 to 50 Gauß) generated by a function current generator in one or more—primary—outer current coils into which the part of the body provided with the osteosynthesis means is inserted. These electromagnetic fields of extremely low frequency pass through the tissue practically with no loss, including any clothing and a plastercast, as well as the non-magnetic (austenitic) supporting metals of the osteosynthesis. In electrical contact therewith a—secondary—coil assembly, the so-called transmitter, is implanted. The electrical potentials induced in the transmitter are thus brought into effect in the region of the bone lesion as well as generally in the tissue bordering the means of osteosynthesis.

This technique of inductive transmission of therapeutically effective electrical potentials to the components of the osteosynthesis avoids the risk of infection by percutane electrical conductors and the treatment parameters voltage, frequency, intensity, signal shape and treatment time with indication-specific programming of a function current generator of the induced magnetic field can be determined.

SUMMARY OF THE INVENTION

The invention is based on the object of improving a generic intramedullary nail system particularly as regards its handling convenience and flexible application during the operation, its stability, its biological effect, its therapeutical effectiveness and its economy.

This object is achieved by the features of the independent claims.

Advantageous embodiments of the invention read from the dependent claims.

The invention is an improvement over the generic intramedullary nail system in that the coil assembly is now provided in an end cap assembly proximally releasably connected to the nail member with an outer contact surface being electrically conductive at least in part, that the contact surface is electrically insulated from the nail member, that at least one section of the contact surface forms the first electrode and that at least one section of the nail member forms the second electrode. Whilst in the generic intramedullary nail system the transmitter is arranged within the nail member cavity, a different arrangement is selected in the present invention, namely in a housing of an end cap brought into contact with the nail member in conclusion of the implantation. This now makes it possible to implant the nail member without being influenced by the electrical components. More particularly, the use of a guiding skewer is not obstructed or made impossible by components arranged in the nail member cavity. The guiding skewer is introduced conventionally into the broken bone, for example the tibia and the intramedullary nail can now be subsequently guided into place directly, after which the guiding skewer is removed and distal and/or proximal locking screws can be applied which penetrate the nail through facing apertures to achieve an additional stability in rotation. To conclude implantation the end cap, the housing of which contacts a pole of the coil assembly is connected to the nail member. In this arrangement an electrical contact is produced particularly between the other pole of the coil assembly and the nail member so that the contact surface of the end cap assembly and the nail member form an electrode pair. In addition to the advantages as regards application of a guiding skewer it is to be noted that the nail member is not weakened by any recesses, such as routings for receiving electrical components, resulting in the nail member retaining the stability it would have had also in the conventional "non-electric" case which makes for a considerable reduction in the probability of a nail fracture. This reduction is further enhanced by the advantageous effect of the electrical potentials shortening the healing process. The end cap in accordance with the invention thus has a dual function. For one thing, it prevents growth of the connective tissue and bone into the nail member which would complicate explantation of the nail member. For another, the end cap accommodates the components which endow the intramedullary nail system with its electrical properties. In addition to the aforementioned advantages as regards continued use of a nail member practically unchanged, it is furthermore to be noted that the surgeon can now decide during the operation whether to close off the nail member with a normal end cap or an end cap fitted with the electrical components. In addition to this providing and shelving magnetically inducible end caps is much less complicated and thus more cost-effective than providing magnetically inducible nail members with the necessary differing dimensions. Further biological advantages are: the risk of infection is now diminished by intensified blood circulation and an immune reaction of the stimulated tissue in overcoming the resistance to antibiotics of multiresistant *staphylococcus Aureus* (MRSA) whilst avoiding the adherence of bacterial films to the surface of the nail member due to electrical activation of the surface by magnetic induction.

The invention has the further advantageous embodiment that the end cap assembly features an electrically conductive end cap housing, the surface of which forms the contact surface. For example, the end cap housing can be made of the same material as the nail member. The electrical components arranged in the end cap housing are preferably potted in an electrically insulating plastics material, for example, epoxy resin. In addition or as an alternative to the epoxy resin potting, the proximal end of the end cap housing can be closed off by an electrically conductive or insulating cover. It is not necessary to realize the full surface of the electrically conductive end cap housing as an electrode. In a preferred, at least portionally cylindrical end cap assembly a ring electrode may be provided for example surrounding the cylindrical sheath, whereby the ring electrode is connected via an insulating layer to the part of the end cap housing not acting as an electrode. For example, the ring electrode may be inset in the end cap housing so that a smooth outer surface is made available.

Particularly when the complete end cap housing forms an electrode is it usefully provided for that the end cap assembly and the nail member are connected threaded endowed with an insulating layer. The end cap together with its threaded portion can thus be made of a uniform electrically conductive material to facilitate production and by the use of metal threads ensures a rugged connection between nail member and end cap. The necessary insulation between end cap and nail member is provided by an insulating layer fixedly connected to the nail member or to the end cap, it being just as possible, however, to provide the insulating layer as a separate element before mounting the end cap. In relinquishing the advantages of an end cap of uniform material, it is also possible to make the portion of the end cap including the thread of an insulating material.

In accordance with an alternative embodiment of the invention it is provided for that the end cap assembly comprises an electrically insulating end cap housing as well as, for closing off the end cap housing, an electrically conductive cover, the surface of which forms the contact surface. Suitable materials for the end cap housing are, for example, polyethylene, for instance of the kind as also used for sockets in the scope of endprothetics.

In a particularly advantageous further embodiment of the invention the second pole of the coil is connected via an elastically electrical contact to an electrically conductive element inserted in the cavity of the nail member, the element being electrically conductive connected to the nail member. This elastically electrical contact via, for example, a coil spring, a leaf spring or the like ensures a good electrical conductivity in the contact portion. Before screwing on the end cap an electrically conductive element is inserted into the nail member, after which the end cap is screwed on and an elastically electrical contact arranged preferably centrally at the distal end of the end cap produces the contact of the second pole of the coil assembly to the nail member. The insert is thus secured in the nail member so that at least any axial displacement is prevented distally. It is in this way that the insert offers the force necessary to counter deformation of the electrical contact promoting electrical contacting.

For example, it may be provided for that the insert is a compression screw via which a stud penetrating two facing slots in the nail member can be subjected to an axially directed force. The compression screw is urged against a stud located in the slots, resulting in the bone fragments in the region of the fracture gap being compressed together. When the fracture is axially stable, this results in an active, biomechanically favorable circumferential compression of the fracture fragments, it being particularly in this way that the axial loading is transmitted to the bone, relieving the nail member. In conjunction with the present invention the compression screw has a dual function. In addition to its compressive function the compression screw becomes part of the electrical system by it namely producing the contact between the second pole of the coil assembly and the nail member acting as an electrode.

In a particularly advantageous further embodiment of the invention the coil assembly is connected to the contact surface via an electrical rectifier in such a way that the first electrode formed by the contact surface has a positive polarity, at least mainly. This results in the magnetically induced osteogenesis being concentrated on the stabilization portion of the intramedullary nail system, i.e. the nail member, since the osteogenesis depends on the polarity of the corresponding electrodes, it namely being promoted at the cathode and obstructed at the anode, as a result of which bone formation in the ambience of the end cap is obstructed, prevented and/or an osteolysis is caused, whilst in the region of the fracture bone formation is promoted as desired. This in particular simplifies explantation of the intramedullary nail system since the end cap can be simply removed for the purpose of the explantation without this being obstructed by bone tissue. Due to the magnetically induced osteogenesis in the ambience of the nail member, reestablishing the mechanical loading capacity of the bone is accelerated, as a result of which the surgical method of converting a static interlock of the healing bone can be converted into a dynamic interlock by removing the proximal locking screws at an earlier point in time. This applies also to the point in time of removing the intramedullary nail system as a whole.

It can be provided for that an ohmic resistance is provided connected in parallel to the rectifier. It may likewise be provided for that a capacitive resistance is provided in parallel to the rectifier to thus achieve an incomplete rectifier so that parameters are available for setting the suitable conditions as regards osteogenesis and osteolysis.

It is expediently provided for that the coil assembly comprises a coil core, by means of which—for example a soft magnetic ferrite core—the electric power can be increased for a given external magnetic field strength. In maintaining the electric power the work can be done with lower magnetic field strengths and or smaller components.

It may furthermore be provided for that at least one elongated soft magnetic element is inserted into the nail member. This arrangement of the soft magnetic material in the nail member concentrates the magnetic field as applied externally which is also effective in the region of the end cap so that with the given transmission capacity a higher electric power is available. For a given magnetic alternating field a desired electric power can be made available in using a smaller transmitter so that less room is needed for the transmitter, in thus enabling the intramedullary nail system in accordance with the invention to be realized with smaller end caps In accordance with a further preferred embodiment it may be provided for that at least one elongated unsaturated permanent magnetic element is inserted into the nail member. The electric fields generated via the surface electrodes at the nail member and at the end cap penetrate the ambient tissue only slightly in depth, amounting to just a few cell diameters usually. Providing a permanent magnetic element generates a magnetic field also in regions of the tissue further remote from the implant, this magnetic field becoming weaker the further it is away radially from the permanent magnetic element. Due to the presence of this gradient in the magnetic field, electric fields can be induced in the tissue due to the movement of the tissue, indeed with a significantly greater distance away from the implant than is possible on the basis of the surface electrodes, in thus also promoting the healing process at a greater distance away from the implant. The permanent magnetic element is magnetic unsaturated so that the magnetization thereof can follow partly the alternating field applied externally. This makes sure that no undesirable total concentration of the magnetic field applied externally occurs at the region surrounding the permanent magnetic element. Instead, an adequate magnetic field can be made available in the region of the transmitter in the end cap. The unsaturated permanent magnetic element can thus be inserted to advantage in combination with a soft magnetic element.

It is expediently provided for that the at least one electrode element is surrounded by an insulating sheath as may be formed, for example, by shrink tubing sheathing the element fluid and gas-tight.

It may also be provided for that several elongated elements are surrounded by one and the same insulating sheath. When, for example, several soft magnetic elements or several unsaturated permanent magnetic elements or also combinations thereof are inserted, these can also be sheathed by a single insulating sheath in thus making it possible to make the insertion during the operation by a single manipulation.

Yet a further particularly useful embodiment of the invention provides for the outer surface of the nail member featuring an electrically conductive coating, at least in part, enlargening the surface of the nail member in avoiding bacterial colonization. Known are bactericidal coatings. Selecting an electrically conductive biologically compatible which enlargens the surface of the nail member increases the bactericidal effect, namely due to the enlargened surface for transmitting the electric field to the ambient tissue.

In this context preferably the coating comprises silver. A silver coating, for example, can be applied directly to implants of steel or titanium alloys namely by means of sputtering.

However, it may also be provided for expediently that a porous interlayer is provided between the surface of the nail member and the coating. The electrically conductive connection of the coating to the surface of the nail member located under the insulating layer is made available by the ambient body fluid and or by direct contact of the silver particles with the surface. The porous interlayer comprises, for example, a ceramic or plastics material.

The invention relates furthermore to a nail member suitable for being used together with an intramedullary nail system in accordance with the invention.

The invention furthermore involves an end cap assembly suitable for being used together with an intramedullary nail system in accordance with the invention.

BRIEF DESCRIPTION OF THE DRAWINGS

The invention will now be detained by way of preferred embodiments with reference to the attached drawings in which.

DETAILED DESCRIPTION OF THE INVENTION

Figure 1:
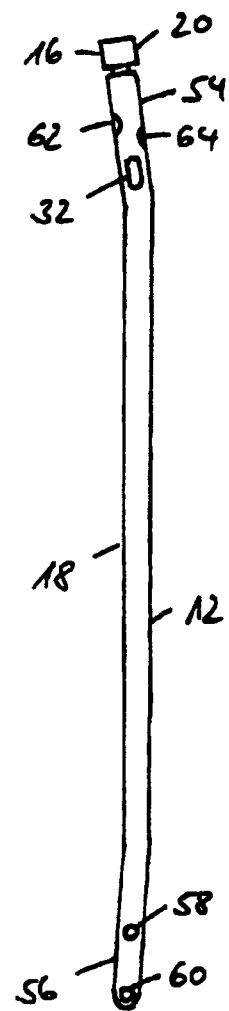
FIG. 1 is a side view of an intramedullary nail system in accordance with the invention.

In the following description of preferred embodiments of the present invention like reference numerals identify like or comparable components.

Figure 2:
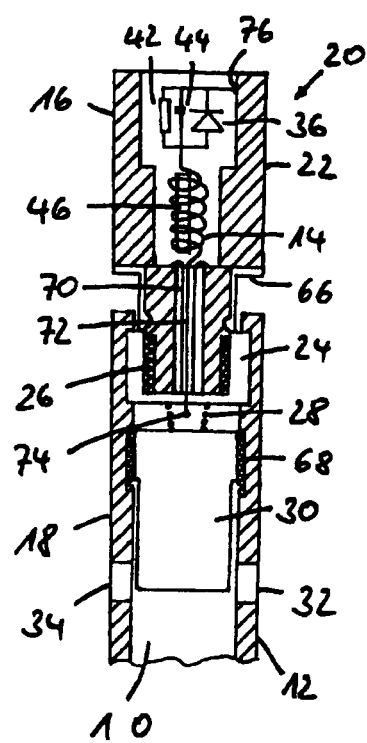
FIG. 2 is a section taken axially through the proximal end portion of a first embodiment of an intramedullary nail system in accordance with the invention.

Referring now to FIG. 1 there is illustrated a side view of an intramedullary nail system in accordance with the invention; FIG. 2 showing a section taken axially through the proximal end portion of a first embodiment of an intramedullary nail system in accordance with the invention. Illustrated is an intramedullary nail system for stabilizing and resting fragments of a broken bone for example of the tibia, the femur or humerus. The intramedullary nail system comprises a more or less cylindrical nail member 12 and an end cap assembly 20 closing off an opening of the nail member 12 at its proximal end 54 substantially axially symmetrically. The nail member 12 has at its distal end 56 likewise an opening (not shown). The openings at the proximal end 54 and distal end 56 are connected to each other by a cavity 10 in the nail member 12. Provided in the wall of the nail member are locking apertures 58, 60, 62, 64 each of which faces a further locking aperture diametrally opposed. The one group of locking apertures 58, 60 is arranged at the distal end 56 whilst the other group of locking apertures 62, 64 is provided at the proximal end 54. Likewise provided at the proximal end 54 of the nail member 12 is a pair of slots 32, 34 facing each other diametrally opposed.

The intramedullary nail system as shown in FIG. 1 finds application in the scope of osteosythesis as follows: firstly, a guiding skewer (not shown) is introduced into the cavity of a fractured tubular bone through the fracture gap. Then, the nail member 12 is guided over the guiding skewer into the tubular bone after which the guiding skewer can be removed. Via the locking apertures 58, 60, 62, 64 one or more locking screws penetrating the bone shank can be inserted which give the bone stabilized by the nail member 12 additional rotational stability. A further stud can be inserted through the slots 32, this serving axial compression of the fracture gap by namely screwing a compression screw 30 into the female thread of the nail member and which is supported at its distal end by the stud located in the slots 32, 34. To conclude the implantation an end cap assembly 20 is applied to the nail member 12, preferably via a threaded portion 26 formed by a male thread on the end cap assembly 20 in a female thread of the nail member.

Referring now to FIG. 2 there is illustrated in particular how the end cap assembly 20 contains a coil assembly 14, and when the end cap assembly 20 is screwed in place it itself acts as an electrode whilst the nail member 12 forms the opposite electrode. The coil assembly 14 is arranged in a free space of the end cap housing 22. The coil assembly 14 surrounds a soft iron core provided to concentrate the magnetic alternating field applied externally. One pole of the coil assembly 14 contacts via a parallel circuit of a diode 36, ohmic resistance 42 and capacitive resistance 44 a contact point 76 of the end cap housing 22. The rectifier circuit realized by the diode 36 can localize bone growth to advantage by the surface of the end cap housing 22 becoming the anode retarding bone growth or at which even osteolysis occurs, whilst the nail member 12 becomes the cathode so that bone growth is promoted particularly in the region of the fracture. The components connected in parallel to the diode 36, i.e. the ohmic resistance 42 and the capacitive resistance 44 are optional, they—as compared to the non-rectified voltage—shifting the voltage curve in the direction of the positive polarity to result in an incomplete rectification. When doing away with the cited advantages of rectification the diode can be eliminated so that the first pole of the coil assembly 14 can be brought into contact with the end cap housing 22 directly. The other pole of the coil assembly 14 is in electrical contact with a coil spring 28 via a contact point 74. For this purpose an electrical conductor 72 is guided through a distal portion of the end cap housing, an insulation 70 preventing thereby an electrical short-circuit of the coil assembly. Machined in the distal portion of the end cap assembly 20 which is tapered as compared to the proximal portion is a screw thread. Via a threaded portion 26 the end cap assembly 20 is screwed into the nail member 12, an insulation 24 preventing thereby an electrical short-circuit of the coil assembly. This insulation 24 is continued proximally to advantage, for example up to the insulation 66 at the transition between the proximal and distal portion of the end cap assembly 20. Screwed into the nail member 12 furthermore is a compression screw 30 via a threaded portion 68. As aforementioned, this compression screw 30 serves to axially load a stud passing through the slots 32, 34 to result in compression in the region of the fracture gap. In this context the compression screw 30 serves furthermore to electrically contact the coil spring 28 which is supported at its proximal end by the insulation 24 and at its distal end by the compression screw 30. Electrical contact between the coil assembly 14, i.e. particularly the contact point 74, and the interior of the end cap housing 22 is produced via the threaded portion 68 and, where necessary, via the stud (not shown) passing through the slots 32, 34.

The electrical components in the interior of the end cap housing 22 are potted in a biologically compatible epoxy resin for electrical insulation and mechanical stability.

Figure 3:
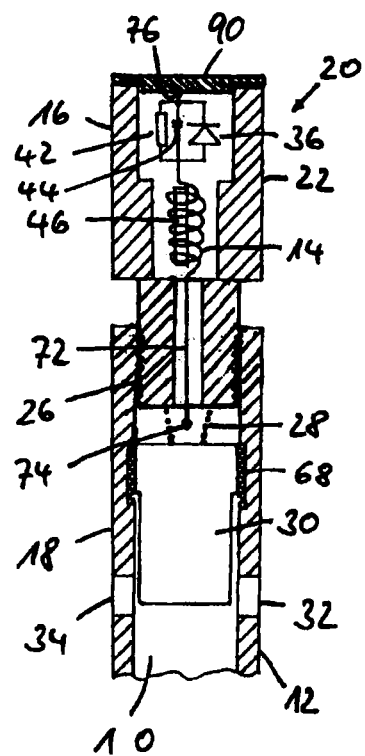
FIG. 3 is an axial section through the proximal end portion of a second embodiment of an intramedullary nail system in accordance with the invention.

Referring now to FIG. 3 there is illustrated an axial section through the proximal end portion of a second embodiment of an intramedullary nail system in accordance with the invention wherein, unlike the embodiment as shown in FIG. 2, an end cap housing 22 of an electrically insulating material, for example biologically compatible polythene is employed. The contact surface is formed by an electrically conductive cover 90 which closes off the end cap housing 22 at its proximal end. The cover 90 can be connected to the end cap housing by being bonded, screwed or clipped in place for instance. When the cover 90 is connected to the end cap housing 22 gas and fluid-tight there is no need to pot the interior of the housing, although still possible, for example for mechanical stabilization of the electrical components and connections. The insulations 24, 26, 70 insulating the end cap housing 22 from the nail member as described in conjunction with FIG. 2 can be dispensed with when an electrically insulating end cap housing 22 is provided as shown in FIG. 3.

Figure 4:
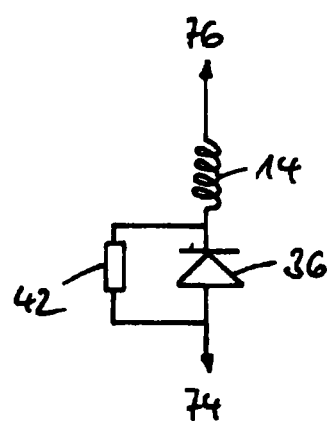
FIG. 4 is block circuit diagram of a rectifier circuit in a first embodiment for use in conjunction with the invention.
Figure 5:
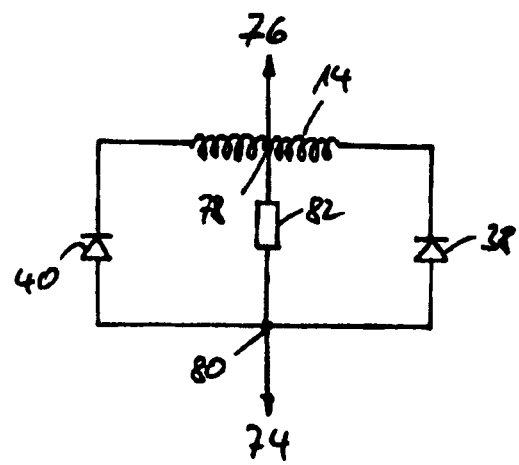
FIG. 5 is block circuit diagram of a rectifier circuit in a second embodiment for use in conjunction with the invention.

Referring now to FIGS. 4 and 5 there are illustrated two embodiments of a rectifier circuit for use in conjunction with the invention. The circuit as shown in FIG. 4 corresponds substantially to the circuit as already described with reference to FIG. 2 except for now involving a capacitive resistance. Depending on the particular application, connecting in parallel an ohmic resistance 42 can also be dispensed with. Whilst FIG. 4 shows a one-way rectifier circuit, shown in FIG. 5 is a two-way rectifier circuit. The coil assembly 14 is center tapped at 78 connected via an ohmic resistance 82 to a circuit node 80 leading to the contact point 74 at the nail member 12 and coil spring 28 respectively. The center tap 78 is furthermore directly connected to the contact point 76 at the end cap housing. Connected to the circuit node 80 are two diodes 38, 40 which contact the two end points of the coil assembly. Here too, the same as already explained with reference to FIGS. 2 and 3, the two-way rectifier circuit as shown in FIG. 5 can also be modified by resistors influencing the AC response of the circuit.

Figure 6:
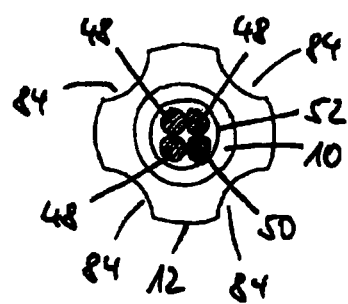
FIG. 6 is a radial section through a nail member of an intramedullary nail system in accordance with the invention with magnetic rods arranged therein.

Referring now to FIG. 6 there is illustrated a radial section through a nail member of an intramedullary nail system in accordance with the invention with magnetic rods arranged therein. The nail member 12 features several recesses 84 extending along its circumference axially for rotational stability of the nail member 12 in the bone. Provided in the cavity 10 of the nail member 12 is an insulating sheath 52 with four rods 48, 50 arranged therein. In the present example three rods 48 of soft magnetic material and a rod 50 of unsaturated permanent magnetic material are involved. Other variants are just as possible, namely by varying the number of rods or exclusively providing soft magnetic material or exclusively providing unsaturated permanent magnetic material. The soft magnetic rods 48 bunch the magnetic alternating field applied externally for focussed concentration thereof effective up to the region of the coil assembly 14 provided in the end cap assembly 20, as a result of which the soft magnetic rods 48 have a concentrating effect on the electric power made available via the tissue electrodes. The unsaturated permanent magnetic rod 50 is able to partly follow the magnetic alternating field applied externally so that—unlike with a saturated permanent magnetic rod—a "short-circuit" of the magnetic field is prevented. The special effect of the permanent magnetic element in the absence of an external magnetic field is namely to provide a magnetic gradient field penetrating the tissue portion surrounding the nail member 12 and which is reduced radially outwards. It is on the basis of this permanently existing magnetic field and the movements of tissue perpendicular to the permanent magnetic field that electric fields are induced in the tissue which promote the healing process. Contrary to the electric field penetrating just a few cell diameters into the tissue as generated by the surface electrodes, the permanent magnetic field penetrates deeply into the tissue inducing electric fields promoting here too the healing process. An external magnetic alternating field can cause the permanent magnet to vibrate, additionally promoting the healing process to advantage.

Figure 7:
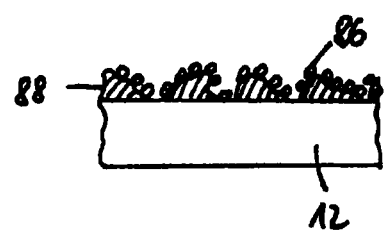
FIG. 7 is a section through the surface of a nail member of an intramedullary nail system in accordance with the invention with a coating enlargening the surface.

Referring now to FIG. 7 there is illustrated a section through the surface of a nail member of an intramedullary nail system in accordance with the invention with a coating enlargening the surface. The outer surface of the nail member 12 is provided with a electrically conductive coating enlargening the surface and preventing colonization of bacteria and comprising silver particles 26 preferably in the colloidal condition. The coating of the surface is imparted by a porous interlayer 86 of plastics or ceramic material, for example. It is, however, just as possible that silver particles are embedded additionally or as an alternative in the porous interlayer as may be realized by applying a ceramic-silver emulsion. The electrical contact between the surface of the nail member 12 and the electrical conductive coating 86 is made available by body fluid or by direct contact of the surface of the nail member 12 with the coating 86 in the region of the pores of the porous surface 88. Due to the bactericidal coating 86 colonization of bacteria is prevented also without the electrical potentials made available over the surface of the nail. This effect is enhanced in the scope of the present invention by the induced electric fields. The effect of the induced electric field on the ambient tissue is further promoted by the contact surface between tissue and electrode being enlargened by the electrically conductive coating 86. The outcome of all this is that the positive biological effects can be enhanced or—whilst still maintaining a given quality—devices can now be made available simpler and more compact, especially as regards the coil assembly and the items generating the external magnetic alternating field.

It is understood that the features of the invention disclosed in the present description, in the drawings and as claimed may be essential both singly and in any combination to achieving the invention.

LIST OF REFERENCE NUMERALS 10 cavity
12 nail member
14 coil assembly
16 first electrode
18 second electrode
20 end cap assembly
22 end cap housing
24 insulating layer
26 threaded portion
28 elastic electrical contact
30 compression screw
32 slot
34 slot
36 diode
38 diode
40 diode
42 ohmic resistance
44 capacitive resistance
46 coil core
48 soft magnetic rod
50 unsaturated permanent magnetic element
52 insulating sheath
54 proximal end
56 distal end
58 locking aperture
60 locking aperture
62 locking aperture
64 locking aperture
66 insulation
68 threaded portion
70 insulation
72 electrical conductor
74 contact point
76 contact point
78 center tap
80 circuit node
82 ohmic resistance
84 recesses
86 electrically conductive coating
88 porous interlayer
90 cover

What is claimed is:

1. An intramedullary nail system designed for use with an externally generated magnetic field, comprising:
   (a) an elongated intramedullary nail member which is electrically conductive at least in part to be inserted into a medullar cavity of a bone, the elongated intramedullary nail member comprising a cavity,
   (b) a coil assembly for generating an electrical voltage between a first and a second electrical coil contact of the coil assembly, the electrical voltage being induced by the externally generated magnetic field,
   (c) a first electrode connected to the first electrical coil contact of the coil assembly, and
   (d) a second electrode connected to the second electrical coil contact of the coil assembly, wherein:
      the coil assembly is provided within an end cap assembly that is proximally releasably connected to the intramedullary nail member with an outer contact surface being electrically conductive at least in part,
      the outer contact surface is electrically insulated from the intramedullary nail member,
      at least one section of the outer contact surface forms the first electrode, and
      at least one section of the intramedullary nail member forms the second electrode.

2. The intramedullary nail system as set forth in claim 1, characterized in that the end cap assembly features an electrically conductive end cap housing, the surface of which forms the contact surface.

3. The intramedullary nail system as set forth in claim 1, characterized in that the end cap assembly and the nail member are connected via a threaded connection as imparted by an insulating layer.

4. The intramedullary nail system as set forth in claim 1, characterized in that the end cap assembly comprises an electrically insulated end cap housing and an electrically conductive cover with a surface which forms the contact surface.

5. The intramedullary nail system as set forth in claim 1, characterized in that the second electrical coil contact of the coil is connected via an elastically electrical contact to an electrically conductive element inserted in the cavity of the nail member, the element being electrically conductive connected to the nail member.

6. The intramedullary nail system as set forth in claim 5, characterized in that the electrically conductive element comprises a compression screw adapted to be subjected to an axially directed force via a stud penetrating two facing slots in the nail member.

7. The intramedullary nail system as set forth in claim 1, characterized in that the coil assembly is connected to the contact surface via an electric rectifier so that the first electrode formed by the contact surface has a positive polarity.

8. The intramedullary nail system as set forth in claim 7, characterized in that the electric rectifier includes an ohmic resistance element connected in parallel thereto.

9. The intramedullary nail system as set forth in claim 7, characterized in that the electric rectifier includes a capacitive resistance element connected in parallel thereto.

10. The intramedullary nail system as set forth in claim 1, characterized in that the coil assembly comprises a coil core.

11. The intramedullary nail system as set forth in claim 1, characterized in that at least one elongated soft magnetic element is inserted into the nail member.

12. The intramedullary nail system as set forth in claim 1, characterized in that at least one elongated unsaturated permanent magnetic element is inserted into the nail member.

13. The intramedullary nail system as set forth in claim 1, characterized in that the elongated nail member includes at least one elongated magnetic element that is surrounded by an insulating sheath.

14. The intramedullary nail system as set forth in claim 1, characterized in that elongated nail member includes a plurality of magnetic elongated elements, wherein the plurality of magnetic elongated elements are surrounded by an insulating sheath.

15. The intramedullary nail system as set forth in claim 1, characterized in that the outer surface of the nail member further includes an electrically conductive coating adapted to enlarge at least part of the surface of the nail member and aiding in the prevention of bacterial colonization.

16. The intramedullary nail system as set forth in claim 15, characterized in that the coating comprises silver.

17. The intramedullary nail system as set forth in claim 15, characterized in that a porous interlayer is provided between the surface of the nail member and the coating.

18. A nail member for use in an intramedullary nail system according to claim 1, further including an electrically conductive element inserted in the cavity and electrically coupled thereto.

19. The nail member as set forth in claim 18, characterized in that the electrically conductive element comprises a compression screw adapted to be subjected to an axially directed force via, a stud penetrating two facing slots in the nail member.

20. An intramedullary nail system designed for use with an externally generated magnetic field comprising;
    (a) an elongated nail member which is electrically conductive at least in part to be inserted in a medullar cavity of a bone, wherein the elongated nail member comprises a cavity extending throughout the whole length of the elongated nail member,
    (b) a coil assembly,
    (c) a first electrode connected to a first electrical coil contact of the coil assembly, and
    (e) a second electrode connected to a second electrical coil contact of the coil assembly, wherein;
        the coil assembly is provided in an end cap assembly proximally releasably connected to the nail member with an outer contact surface being electrically conductive at least in part,
        the outer contact surface is electrically insulated from the nail member,
        at least one section of the outer contact surface forms the first electrode,
        at least one section of the nail member forms the second electrode, and
        the coil assembly is connected to the outer contact surface via an electric rectifier so that the first electrode formed by the outer contact surface has a positive polarity.

* * * * *